(12) United States Patent
Cole et al.

(10) Patent No.: US 11,052,207 B2
(45) Date of Patent: Jul. 6, 2021

(54) GAS SENSING APPARATUS

(71) Applicant: KONINKLIJKE PHILIPS N.V., Eindhoven (NL)

(72) Inventors: Kenneth E. Cole, New Alexandria, PA (US); Mark Wayne Barclay, Saxonburg, PA (US); Ljubisa Milojevic, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 383 days.

(21) Appl. No.: 15/768,335

(22) PCT Filed: Oct. 13, 2016

(86) PCT No.: PCT/IB2016/056116
§ 371 (c)(1),
(2) Date: Apr. 13, 2018

(87) PCT Pub. No.: WO2017/068465
PCT Pub. Date: Apr. 27, 2017

(65) Prior Publication Data
US 2018/0296781 A1    Oct. 18, 2018

Related U.S. Application Data

(60) Provisional application No. 62/244,888, filed on Oct. 22, 2015.

(51) Int. Cl.
*A61M 16/00* (2006.01)
*A61M 11/00* (2006.01)
(Continued)

(52) U.S. Cl.
CPC .......... *A61M 16/024* (2017.08); *A61M 11/00* (2013.01); *A61M 16/01* (2013.01);
(Continued)

(58) Field of Classification Search
CPC .............. A61M 16/10; A61M 16/1005; A61M 16/101; A61M 2016/102;
(Continued)

(56) References Cited

U.S. PATENT DOCUMENTS 4,619,269 A * 10/1986 Cutler .................. G01N 33/497
128/204.16
6,884,222 B1    4/2005 Braig
(Continued)

FOREIGN PATENT DOCUMENTS

| EP | 1957139 B1 | 11/2011 |
|---|---|---|
| WO | WO2015127085 A1 | 8/2015 |
| WO | WO2015172160 A1 | 11/2015 |

*Primary Examiner* — Joseph D. Boecker
*Assistant Examiner* — Thomas W Greig
(74) *Attorney, Agent, or Firm* — Daniel H. Brean

(57) ABSTRACT

The present disclosure pertains to an apparatus configured to facilitate monitoring of gas in a therapeutic gas delivery system with a catalytic sensor. The gas delivery system comprises a pressure generator having an inlet and an outlet, and a gas delivery flow path configured to communicate the gas between the pressure generator and a subject. The apparatus comprises a receiver body configured to receive the catalytic sensor such that the catalytic sensor removably couples with the receiver body, the receiver body located remotely from/outside the gas delivery flow path; a delivery port configured receive a portion of gas obtained from the gas delivery system that has passed through the pressure generator outlet and guide the received portion of gas toward the catalytic sensor; and a return port configured to exhaust the received portion of gas from the receiver body to the gas delivery system through the pressure generator inlet.

28 Claims, 5 Drawing Sheets

(51) Int. Cl.
   *A61M 16/08* (2006.01)
   *A61M 16/10* (2006.01)
   *A61M 16/01* (2006.01)
   *A61M 16/06* (2006.01)

(52) U.S. Cl.
   CPC .... *A61M 16/0666* (2013.01); *A61M 16/0883* (2014.02); *A61M 16/1005* (2014.02); *A61M 2016/102* (2013.01); *A61M 2202/02* (2013.01); *A61M 2205/3334* (2013.01)

(58) Field of Classification Search
   CPC ...... A61M 2016/1025; A61M 2202/02; A61M 2202/0208; A61M 2205/3334; A61M 2205/3331; A61M 16/0883; A61M 16/024; A61M 16/01; A61M 11/00; A61M 11/01
   See application file for complete search history.

(56) References Cited

U.S. PATENT DOCUMENTS

| | | |
|---|---|---|
| 2003/0190262 A1 | 10/2003 | Blazewicz |
| 2007/0068528 A1 | 3/2007 | Bohm |
| 2007/0107728 A1 | 5/2007 | Ricciardelli |
| 2010/0041841 A1* | 2/2010 | Terry ................. B01J 8/1827 526/86 |
| 2015/0233879 A1* | 8/2015 | Tolmie ............... G01N 33/0037 128/202.22 |
| 2015/0273175 A1* | 10/2015 | Acker .................. A61M 16/06 128/203.14 |
| 2015/0320951 A1* | 11/2015 | Acker ................ A61M 16/201 128/203.14 |
| 2016/0256656 A1* | 9/2016 | Glenn ............... A61M 16/0057 |

* cited by examiner

GAS SENSING APPARATUS

CROSS-REFERENCE TO RELATED APPLICATIONS

This patent application claims the priority benefit under 35 U.S.C § 371 of international patent application no. PCT/IB2016/05116, filed Oct. 13, 2016, which claims the priority benefit under 35 U.S.C. § 119(e) of U.S. Provisional Application No. 62/244,888 filed on Oct. 22, 2015, the contents of which are herein incorporated by reference.

BACKGROUND OF THE INVENTION

1. Field of the Invention

The present disclosure pertains to an apparatus configured to facilitate monitoring of gas in a therapeutic gas delivery system with a catalytic sensor.

2. Description of the Related Art

Commercially available electro-chemical sensors are available to measure a portion of oxygen present in a gas sample. When oxygen is being delivered to a patient through a respiratory device, the amount of oxygen in the patient airstream being delivered by the device is typically measured by an electro-chemical sensor.

SUMMARY OF THE INVENTION

Accordingly, one or more aspects of the present disclosure relate to an apparatus configured to facilitate monitoring of gas in a therapeutic gas delivery system with a catalytic sensor. The gas delivery system comprises a pressure generator having an inlet and an outlet, a gas delivery flow path configured to communicate the gas between the pressure generator and a subject, and/or other components. The apparatus comprises a receiver body configured to receive the catalytic sensor such that the catalytic sensor removably couples with the receiver body, the receiver body located outside the gas delivery flow path; a delivery port formed by the receiver body configured receive a portion of gas obtained from the gas delivery system that has passed through the pressure generator outlet and guide the received portion of gas toward the catalytic sensor; and a return port formed by the receiver body configured to exhaust the received portion of gas from the receiver body, the return port coupled to the gas delivery system such that the exhausted gas is returned to the gas delivery system through the pressure generator inlet.

Another aspect of the present disclosure relates to a method to facilitate monitoring of gas in a therapeutic gas delivery system with a catalytic sensor and a monitoring apparatus. The monitoring apparatus comprises a receiver body, a delivery port, a return port, and/or other components. The gas delivery system comprises a pressure generator having an inlet and an outlet, a gas delivery flow path configured to communicate the gas between the pressure generator and a subject, and/or other components. The method comprises receiving, with the receiver body, the catalytic sensor such that the catalytic sensor removably couples with the receiver body, the receiver body located outside the gas delivery flow path; receiving, with the delivery port, a portion of gas obtained from the gas delivery system that has passed through the pressure generator outlet and guide the received portion of gas toward the catalytic sensor, the delivery port formed by the receiver body; and exhausting, with the return port, the received portion of gas from the receiver body, the return port coupled to the gas delivery system such that the exhausted gas is returned to the gas delivery system through the pressure generator inlet, the return port formed by the receiver body.

Still another aspect of present disclosure relates to an apparatus configured to facilitate monitoring of gas in a therapeutic gas delivery system with a catalytic sensor. The gas delivery system comprises a pressure generator having an inlet and an outlet, a gas delivery flow path configured to communicate the gas between the pressure generator and a subject, and/or other components. The apparatus comprises means for receiving the catalytic sensor such that the catalytic sensor removably couples with the means for receiving the catalytic sensor, the means for receiving the catalytic sensor located outside the gas delivery flow path; means, formed by the means for receiving the catalytic sensor, for receiving a portion of gas obtained from the gas delivery system that has passed through the pressure generator outlet and guiding the received portion of gas toward the catalytic sensor; and means, formed by the means for receiving the catalytic sensor, for exhausting the received portion of gas from the means for receiving the catalytic sensor, the means for exhausting coupled to the gas delivery system such that the exhausted gas is returned to the gas delivery system through the pressure generator inlet.

Yet another aspect of the present disclosure relates to a therapeutic gas delivery system comprising a pressure generator having an inlet and an outlet configured to generate a pressurized flow of breathable gas for delivery to an airway of a subject; a gas delivery flow path configured to communicate the gas between the pressure generator and the subject; a catalytic sensor configured to generate one or more output signals that convey information related to one or more parameters of the gas; and a monitoring apparatus. The apparatus comprising a receiver body configured to receive the catalytic sensor such that the catalytic sensor removably couples with the receiver body, the receiver body located outside the gas delivery flow path; a delivery port formed by the receiver body configured receive a portion of gas that has passed through the pressure generator outlet and guide the received portion of gas toward the catalytic sensor; and a return port formed by the receiver body configured to exhaust the received portion of gas from the receiver body, the return port coupled to the gas delivery system such that the exhausted gas is returned to the gas delivery system through the pressure generator inlet.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
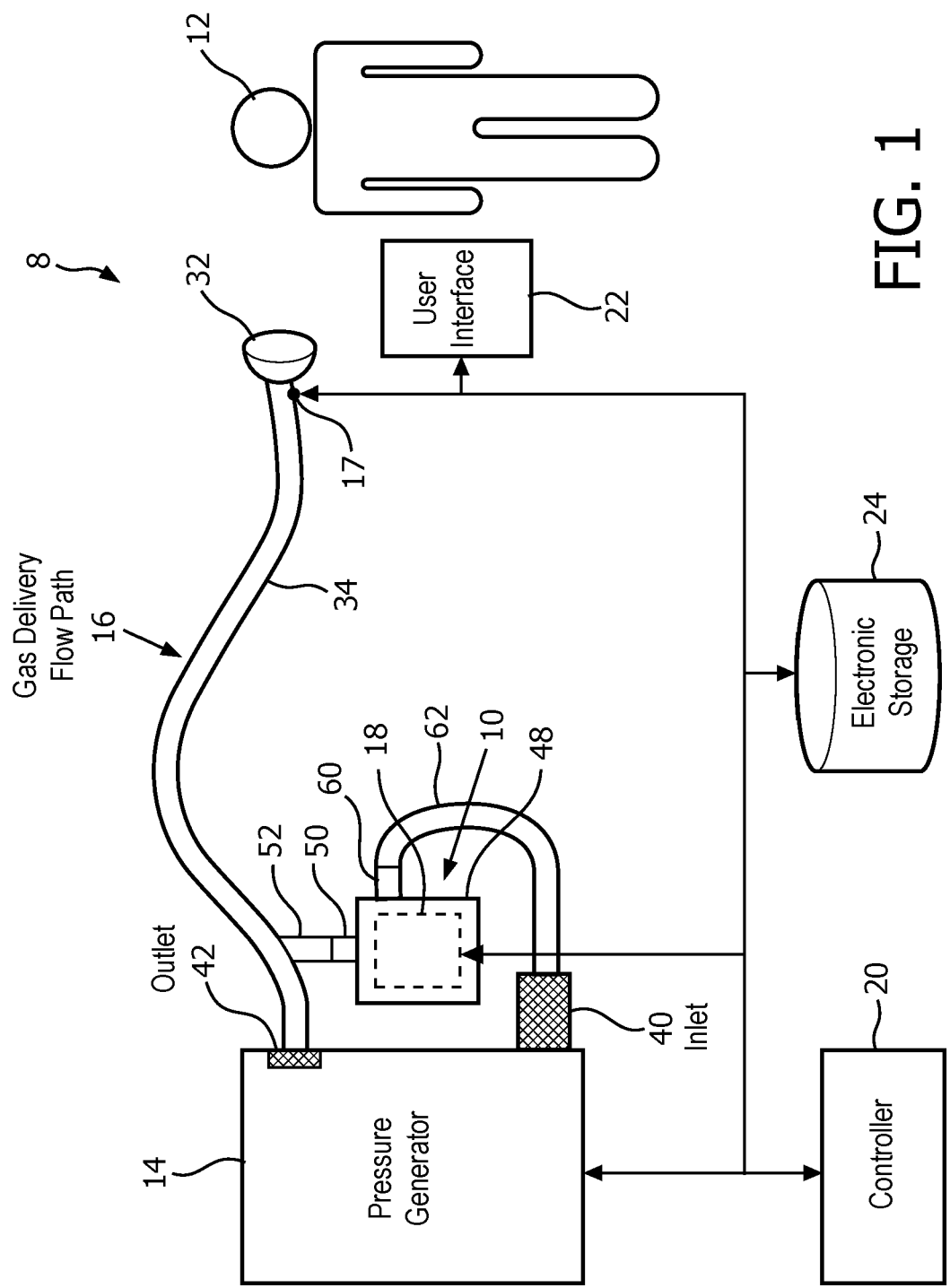
FIG. 1 is a schematic illustration of a therapeutic gas delivery system including an apparatus configured to facilitate monitoring of gas in the system with a catalytic sensor.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a therapeutic gas delivery system 8 including a monitoring apparatus 10 configured to facilitate monitoring of gas in system 8 with a catalytic sensor 18. Traditionally, catalytic sensor 18 must have its sampling port placed directly in the stream of the therapeutic gas delivered to a subject 12. This can create a challenge for physically arranging components of system 8. There must be room to accommodate sensor 18 in an outlet flow path of gas delivered to subject 12. In addition, sensor 18 must remain accessible so that it can be calibrated and/or replaced, for example, by subject 12 and/or other users.

Apparatus 10 is configured such that sensor 18 may be located remotely from/outside a gas delivery flow path 16. Apparatus 10 facilitates the pulling of a pneumatic sample from flow path 16, delivering it to sensor 18, and returning the sample back into system 8. This allows for sensor 18 to be conveniently located where space allows, making it accessible to a user for replacement and/or for other reasons. For example, apparatus 10 is configured such that a small pneumatic tube (e.g., as small as 1/16" inner diameter) "picks" a portion of the flow of gas off at or near a pressure generator (e.g., pressure generator 14 described herein) outlet 42 (positive pressure) and returns the gas (through, e.g., the same sized tubing) at or near a pressure generator 14 inlet 40 (negative pressure). At or near pressure generator outlet 42 may include an area in and/or around pressure generator 14 where the pressure in system 8 is positive. At or near pressure generator inlet 40 may include an area in and/or around pressure generator 14 where the pressure in system 8 is negative (e.g., where gas is about to be, or just recently drawn through pressure generator inlet 40). Returning the sample to a negative pressure area increases the pressure differential (e.g., <0 PSIG) and induces a faster sampling rate through sensor 18.

Figure 2:
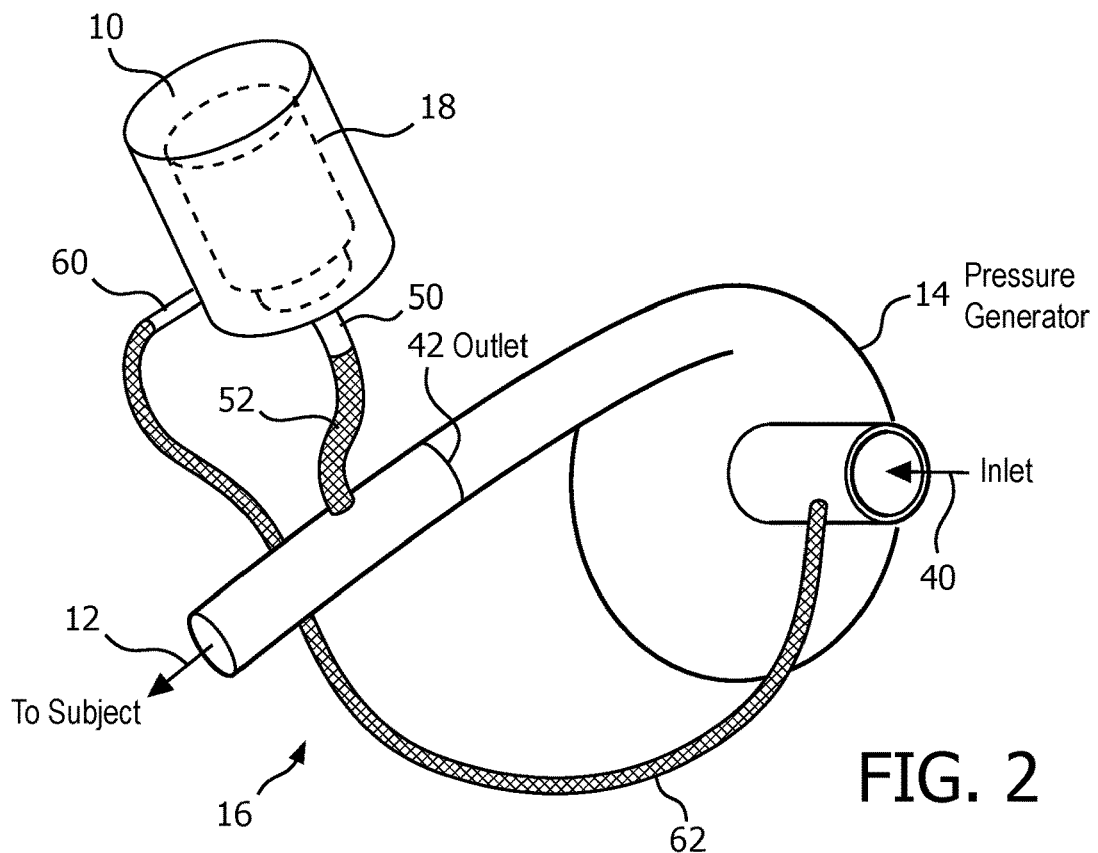
FIG. 2 illustrates an example configuration of a pressure generator, the apparatus, and a sensor.

FIG. 2 illustrates an example configuration of pressure generator 14, apparatus 10, and sensor 18. As shown in FIG. 2, apparatus 10 facilitates remotely locating sensor 18 from flow path 16 and/or locating sensor 18 outside flow path 16 by facilitating the pulling of a pneumatic sample from flow path 16, delivering it via conduit 52 to sensor 18, and returning the sample back into system 8 via conduit 62. These components are further described below.

Returning to FIG. 1, in some embodiments, system 8 comprises one or more of pressure generator 14, gas delivery flow path 16, one or more system sensors 17, catalytic sensor 18, apparatus 10, a controller 20, a user interface 22, electronic storage 24, and/or other components.

Pressure generator 14 is configured to generate a flow of gas for delivery to the airway of a subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the flow rate and/or pressure of the flow of gas to provide pressure support to the airway of subject 12.

Pressure generator 14 receives a flow of gas from a gas source, such as the ambient atmosphere, an external source of therapeutic gas (e.g., oxygen), and/or other sources, and elevates the pressure of that gas for delivery to the airway of subject 12. Pressure generator 14 comprises one or more devices, such as, for example, a pump, blower, piston, bellows, and/or other devices that are capable of elevating the pressure of the received gas for delivery to subject 12. Pressure generator 14 may comprise one or more valves for controlling the pressure/flow of gas. The present disclosure also contemplates controlling the operating speed of a blower included in pressure generator 14, either alone or in combination with such valves, to control the pressure/flow of gas provided to the patient. Pressure generator 14 includes outlet 42 configured to output the pressurized flow of breathable gas for delivery to subject 12. Pressure generator 14 includes inlet 40 configured to receive gas from the therapeutic gas source, draw gas in from the ambient atmosphere, receive gas returning from subject 12, and/or obtain gas for pressurization by other methods.

Gas delivery flow path 16 is configured to communicate the gas between pressure generator 14 and subject 12. As such, gas delivery flow path 16 comprises interface appliance 32, one or more conduits 34, and/or other components. One or more conduits 34 are configured to convey the pressurized flow of gas to interface appliance 32. One or more conduits 34 may comprise a flexible length of hose, and/or other conduits configured to communicate gas between pressure generator 14 and interface appliance 32. Interface appliance 32 is configured to deliver the flow of gas to the airway of subject 12. In some embodiments, interface appliance 32 is configured to be non-invasively engaged by the mouth and/or nose of subject 12. Non-invasive engagement comprises removably engaging one or more external orifices of the airway of subject 12 (e.g., nostrils and/or mouth) to communicate gas between the airway of subject 12 and interface appliance 32. Some examples of non-invasive interface appliance 32 may comprise, for example, a nasal cannula, a nasal mask, a nasal/oral mask, a full face mask, a total face mask, and/or other interface appliances that communicate a flow of gas with an airway of a subject. In some embodiments, interface appliance 32 may include an invasive appliance, such as an endotracheal tube or other invasive appliances. The present disclosure is not limited to these examples, and contemplates delivery of the flow of gas to the subject using any interface appliance.

Although gas delivery flow path 16 is illustrated in FIG. 1 as a single-limbed interface for the delivery of the gas to the airway of subject 12, this is not intended to be limiting. The scope of this disclosure includes double-limbed circuits having a first limb configured to provide the flow of gas to the airway of the subject, and a second limb configured to selectively exhaust gas (e.g., to exhaust exhaled gases). Such a second limb may exhaust gas to the ambient atmosphere and/or may couple interface appliance 32 to inlet 40 of pressure generator 14, for example.

One or more system sensors 17 are configured to generate output signals conveying information related to one or more parameters of the gas within system 8 and/or other information. The one or more parameters of the gas within system 8 may comprise gas parameters related to the pressurized flow of breathable gas, breathing parameters related to respiration of subject 12, and/or other parameters. Sensors 17 may comprise one or more sensors that measure such parameters directly (e.g., through fluid communication with the flow of gas in interface appliance 32). Sensors 17 may comprise one or more sensors that generate surrogate output signals related to the one or more parameters indirectly. For example, sensors 17 may comprise one or more sensors configured to generate an output based on an operating parameter of pressure generator 14 (e.g., flow rate and/or pressure estimations from motor current, voltage, rotational velocity, and/or other operating parameters), and/or other sensors.

The one or more gas parameters of the pressurized flow of breathable gas may comprise, for example, one or more of a flow rate, a volume, a pressure, humidity, temperature, acceleration, velocity, one or more parameters related to a chemical composition of the gas, and/or other gas parameters. Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters.

In some embodiments, sensors 17 include catalytic sensor 18. In some embodiments, sensor 18 is a commercially available catalytic sensor. In some embodiments, sensor 18 is a commercially available oxygen sensor. Sensor 18 is configured to generate output signals conveying information related to concentration of one or more gasses in the therapeutic gas delivered to subject 12 by system 8. For example, sensor 18 may be and/or include an oxygen sensor configured to generate output signals conveying information related to concentration of $O_2$ in the therapeutic gas delivered to subject 12 by system 8. Sensor 18 is coupled to apparatus 10 and located remotely from/outside gas delivery flow path 16. In some embodiments, being located remotely from/outside gas delivery flow path 16 includes being located outside of conduit 34, interface appliance 32, and/or other components of gas delivery flow path 16. In some embodiments, being located remotely from/outside gas delivery flow path 16 includes being located where a user may easily access sensor 18 for adjustment, replacement, and/or other purposes without substantially disturbing pressure generator 14, gas delivery flow path 16, and/or other components of system 10. In some embodiments, the remote location of sensor 18 may enable access to sensor 18 with minimal to no penalty to system 8 as a whole, for example.

Although sensors 17 and 18 are illustrated in FIG. 1 at only two locations in system 10, this is not intended to be limiting. Sensors 17, for example, may comprise sensors disposed in a plurality of locations, such as at various locations within pressure generator 14, within (or in communication with) interface appliance 32, and/or other locations.

Apparatus 10 is illustrated in FIG. 3-6. Apparatus 10 is configured to facilitate monitoring of gas in therapeutic gas delivery system 8. Apparatus 10 comprises a receiver body 48, a delivery port 50, a return port 60, and/or other components.

Figure 3:
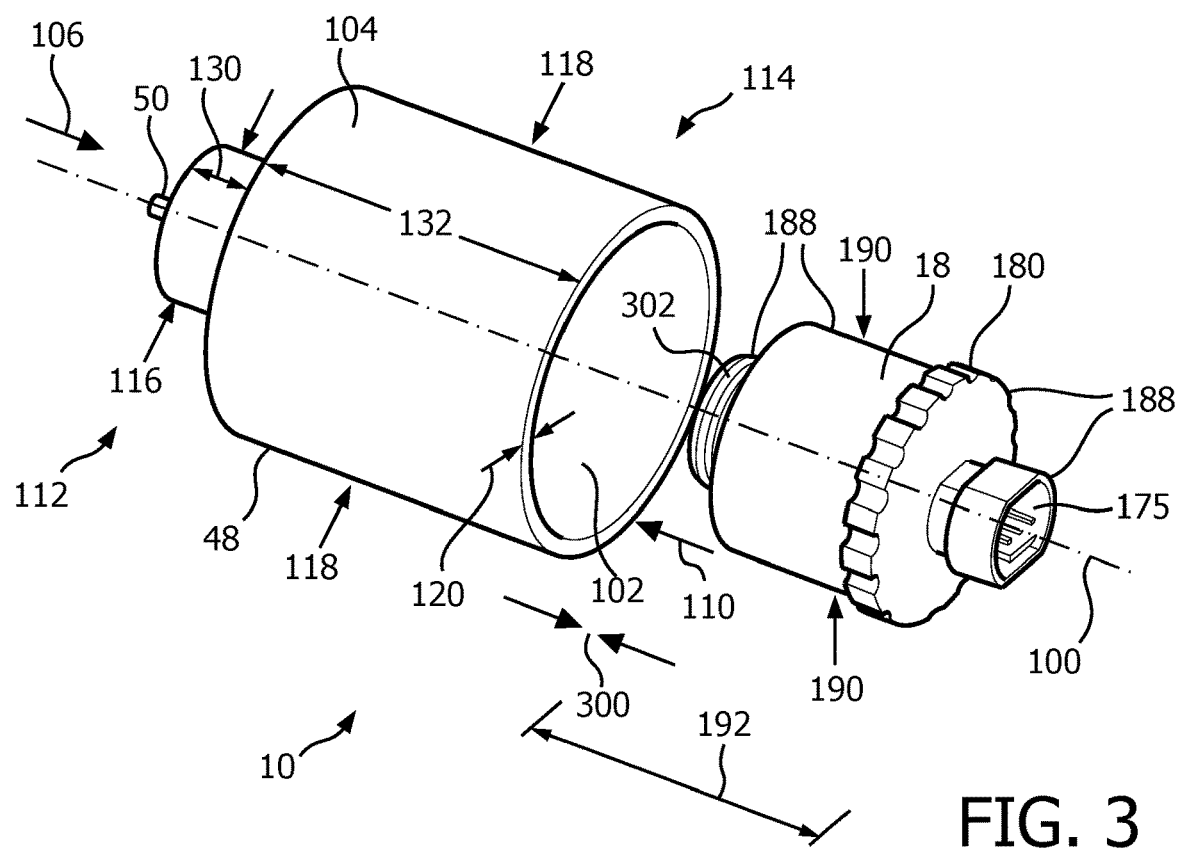
FIG. 3 illustrates the apparatus and the sensor.

As shown in FIG. 3, receiver body 48 is configured to receive sensor 18 such that sensor 18 removably couples 300 with receiver body 48. In some embodiments, receiver body 48 and/or sensor 18 comprise one or more receiving features 302 that facilitate sealing between sensor 18 and receiver body 48. For example, in a respiratory care system such as system 8, the one or more receiving features 302 may include a threaded connection coupled with an O-ring portion and/or other features. Sensor 18 may include other features such as an electrical connector 175, a knurled tightening/loosening portion 180, and/or other features (e.g., these features are typical for commercially available sensors such as sensor 18). As described above, receiver body 48 is located remotely from gas delivery flow path 16 (not shown in FIG. 3-6). Receiver body 48 is configured to receive catalytic sensor 18 (e.g., an $O_2$ sensor) such that catalytic sensor 18 is not in gas delivery flow path 16 of system 8.

In FIG. 3, delivery port 50 and sensor 18 are located along an axis 100 of apparatus 10. Delivery port 50 is located at a first end 106 of receiver body 48. Receiver body 48 is configured to receive sensor 18 via second end 110 of receiver body 48 opposite first end 106 along axis 100. Receiver body 48 is configured to receive sensor 18 in an interior 102 of receiver body 48. Second end 110 of receiver body 48 is open to facilitate receipt of sensor 18 into interior 102. In some embodiments, receiver body 48 includes a first portion 112 located toward first end 106, a second portion 114 located toward second end 110 along axis 100, and/or other portions.

In some embodiments, first portion 112 and second portion 114 have substantially cylindrical cross-sectional shapes. In some embodiments, first portion 112 has an outside diameter 116 of up to about 0.85 inches and a length 130 of up to about 0.65 inches. In some embodiments, first portion 112 has an outside diameter 116 of between about 0.65 and about 0.85 inches, and a length 130 of between about 0.45 and about 0.65 inches. In some embodiments, first portion 112 has an outside diameter 116 of about 0.76 inches and a length 130 of about 0.55 inches. Second portion 114 may have an outside diameter 118 of up to about 1.4 inches and a length 132 of up to about 1.8 inches. In some embodiments, second portion 114 may have an outside diameter 118 of between about 1.2 inches and about 1.4 inches, and a length 132 of between about 1.6 inches and about 1.8 inches. In some embodiments, second portion 114 may have an outside diameter 118 of about 1.31 inches and a length 132 of about 1.7 inches. In some embodiments, receiver body 48 has a wall thickness 120 of up to about 0.2 inches. In some embodiments, receiver body 48 has a wall thickness 120 of between about 0.05 inches and about 0.2 inches. In some embodiments, receiver body 48 has a wall thickness 120 of about 0.1 inches. In some embodiments, wall thickness 120 may vary along first portion 112 and/or second portion 114, and/or may vary from first portion 112 to second portion 114.

It should be noted that the cross-sectional shape(s) and/or dimensions described herein (e.g., in the paragraphs above and below) are not intended to be limiting. Apparatus 10 (receiver body 48, delivery port, return port 60, and/or other components) may have any cross-sectional shape and/or dimensions that allow it to accommodate a shape (e.g., cross-sectional shape 188, diameter 190, length 192, etc.) of sensor 18 so that apparatus 10 and system 8 function as described herein.

Figure 4:
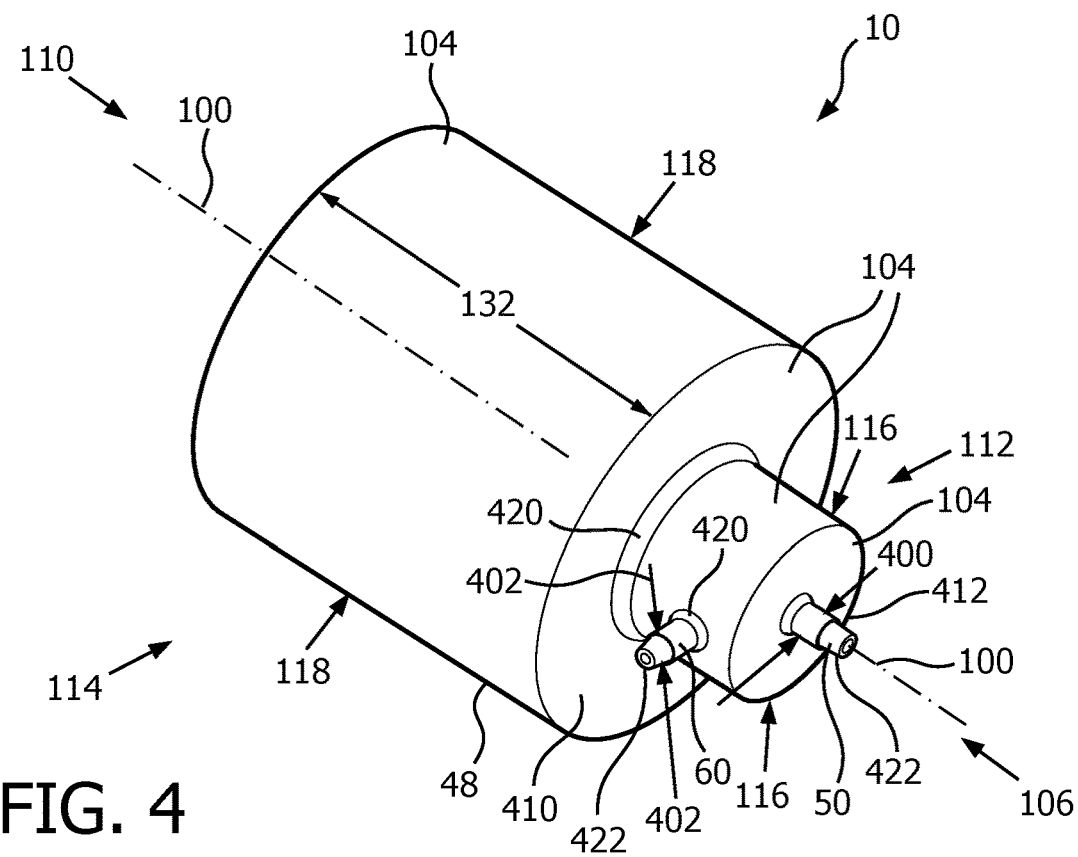
FIG. 4 illustrates a delivery port and a return port of the apparatus.

FIG. 4 illustrates delivery port 50 and return port 60. As shown in FIG. 4, delivery port 50 and return port 60 are formed on exterior 104 of receiver body 48 of first portion 112 toward first end 106. Delivery port 50 is formed along axis 100. Return port 60 is substantially perpendicular to axis 100. This perpendicularity shown in FIG. 4 is not intended to be limiting. Return port 60 may be formed at any angle that allows apparatus 10 to function as described herein. In some embodiments, first portion 112 is formed on a transition surface 410 of second portion 114. In some embodiments, delivery port 50 is formed on an end surface 412 of first portion 112 toward first end 106. In some embodiments, receiver body 48, delivery port 50, and/or return port 60 may include chamfers 420, tapers 422, and/or other features that facilitate coupling with sensor 18, coupling with tubing conducting gas to and/or from system 8, and/or other have other purposes.

Delivery port 50 is configured to receive a portion of gas obtained from gas delivery system 8 that has passed through pressure generator 14 outlet 42 (FIG. 1-2). Delivery port 50 is configured to guide the received portion of gas toward catalytic sensor 18 (FIG. 1-2). Delivery port 50 is configured to receive the portion of gas from gas delivery system 8 via a conduit 52 (FIG. 1-2) having an inner diameter of down to about $\frac{1}{16}^{th}$ of an inch that couples gas delivery system 8 at or near pressure generator 14 outlet 42 with delivery port 50. As such, delivery port 50 has an outside diameter 400 of up to about 0.25 inches. In some embodiments, delivery port 50 has an outside diameter 400 of up between about 0.1 inches and about 0.2 inches. In some embodiments, delivery port 50 has an outside diameter 400 of about 0.118 inches. It should be noted, however, that outside diameter 400 may have any diameter that facilitates coupling with any tubing used to couple system 8 with apparatus 10.

Return port 60 is formed by receiver body 48 and configured to exhaust the received portion of gas from receiver body 48. Return port 60 is configured to facilitate return of the exhausted gas to gas delivery system 8 through pressure generator 14 inlet 40 (FIG. 1-2). Return port 60 is configured to facilitate return of the exhausted gas to gas delivery system 8 via a conduit 62 (FIG. 1-2) having an inner diameter of down to about $\frac{1}{16}^{th}$ of an inch that couples gas delivery system 8 at or near pressure generator 14 inlet 40 with return port 60. As such, return port 60 has an outside diameter 402 of up to about 0.25 inches. In some embodiments, return port 60 has an outside diameter 402 of up between about 0.1 inches and about 0.2 inches. In some embodiments, return port 60 has an outside diameter 402 of about 0.118 inches. It should be noted that, similar to delivery port 50, outside diameter 402 may have any diameter that facilitates coupling with any tubing used to couple system 8 with apparatus 10.

Figure 5:
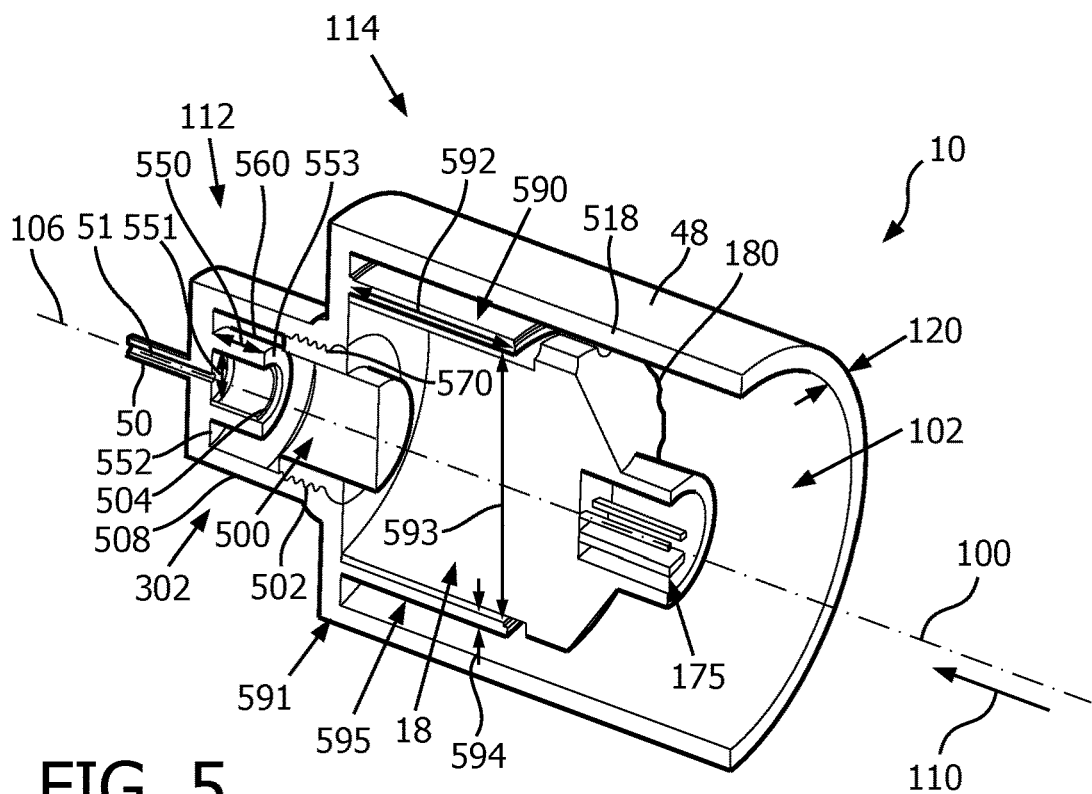
FIG. 5 is a cross-sectional view of the sensor coupled with a receiver body of the apparatus.

FIG. 5 illustrates a cross-sectional view of sensor 18 coupled with receiver body 48. As shown in FIG. 5, delivery port 50 is formed on exterior 104 of receiver body 48 toward first end 106 of receiver body 48 such that delivery port 50 and a sensor face 500 of catalytic sensor 18 are located in proximity to each other toward first end 106. Delivery port 50 forms a channel 51 along axis 100. Channel 51 is configured to guide received gas toward sensor face 500. In some embodiments, channel 51 has a diameter of up to about 0.1 inches. In some embodiments, channel 51 has a diameter of between about 0.01 inches and about 0.1 inches. In some embodiments, channel 51 has a diameter of about 0.045 inches. (It should be noted that return port 60 is also located in proximity to delivery port 50 and sensor face 500 toward first end 106 and forms a channel similar to channel 51 but is not shown in FIG. 5.)

FIG. 5 illustrates receiving features 302 comprising a threaded connection 502 and an O-ring portion 504. Receiving features 302 are located along axis 100 toward second end 110 relative to delivery port 50. Receiving features 302 are configured to facilitate removable and/or other coupling of sensor 18 with apparatus 10. O-ring portion 504 may have a cylindrical cross sectional area and/or other shapes and extend from delivery port 50 toward sensor face 500 along axis 100. In some embodiments, O-ring portion 504 may have a length 550 of up to about 0.225 inches, an inside diameter 551 of up to about 0.235 inches, and a wall thickness 552 of up to about 0.2 inches. In some embodiments, O-ring portion 504 may have a length 550 of between about 0.205 inches about 0.225 inches, an inside diameter 551 of between about 0.215 inches and about 0.235 inches, and a wall thickness 552 of between about 0.05 inches and about 0.2 inches.

In some embodiments, O-ring portion 504 may have a length 550 of about 0.216 inches, an inside diameter 551 of about 0.225 inches, and a wall thickness 552 of about 0.1 inches. In some embodiments, an end 553 of O-ring portion 504 toward sensor face 500 may include one or more surface features (e.g., grooves, depressions, steps, etc.) configured to receive and/or engage an O-Ring. In some embodiments, O-ring portion 504 is formed within first portion 112 of receiver body 48 such that there is a radial space 560 between O-ring portion 504 and a wall 508 of first portion 112. Threaded connection 502 is formed by corresponding threads on sensor 18 near sensor face 500 and in wall 508 of first portion 112 of receiver body 48 toward first end 106. The threads in wall 508 of first portion 112 are formed on an inner surface 570 of wall 508 toward second portion 114 of receiver body 48. In some embodiments, wall 508 has a wall thickness similar to and/or the same as wall thickness 120. In some embodiments, receiving features 302 include coupling mechanisms in addition to and/or instead of threaded connection 502 for coupling sensor 18 with apparatus 10. For example, receiving features may include clips, clamps, screws, nuts, bolts, a hook and eye coupling mechanism, adhesive, tape, and/or other components.

Second portion 114 of receiver body 48 includes a sensor seating guide 590. Sensor seating guide 590 may have a cylindrical cross-sectional area and/or other shapes and extend from a first end 591 of second portion 114 toward second end 110 along axis 100. The shape and/or dimensions of sensor seating guide 590 may correspond to sensor 18 and/or other devices. For example, in some embodiments, sensor seating guide 590 may have a length 592 of up to about 0.705 inches, an inside diameter 593 of up to about 1.2 inches, and a wall thickness 594 of up to about 0.15 inches. In some embodiments, sensor seating guide 590 may have a length 592 of between about 0.685 inches and about 0.705 inches, an inside diameter 593 of between about 1.1 inches and about 1.2 inches, and a wall thickness 594 of between about 0.05 inches and about 0.15 inches. In some embodiments, sensor seating guide 590 may have a length 592 of about 0.695 inches, an inside diameter 593 of about 1.14 inches, and a wall thickness 594 of about 0.1 inches. Length 592 may extend from first end 591 to a location that corresponds to knurled portion 180 of sensor 18 when sensor 18 and apparatus 10 are coupled via threaded connection 502. Diameter 593 may be just large enough to accommodate diameter 190 (FIG. 3) of sensor 18. In some embodiments, sensor seating guide 590 is formed within second portion 114 of receiver body 48 such that there is a radial space 595 between sensor seating guide 590 and a wall 598 of second portion 114. In some embodiments, sensor seating guide 590 is configured to guide sensor 18 into apparatus 10 such that the threads on sensor 18 align with the threads on inner surface of wall 508 of first portion 112. This may make it easier for a user to removably couple sensor 18 with apparatus 10.

Figure 6:
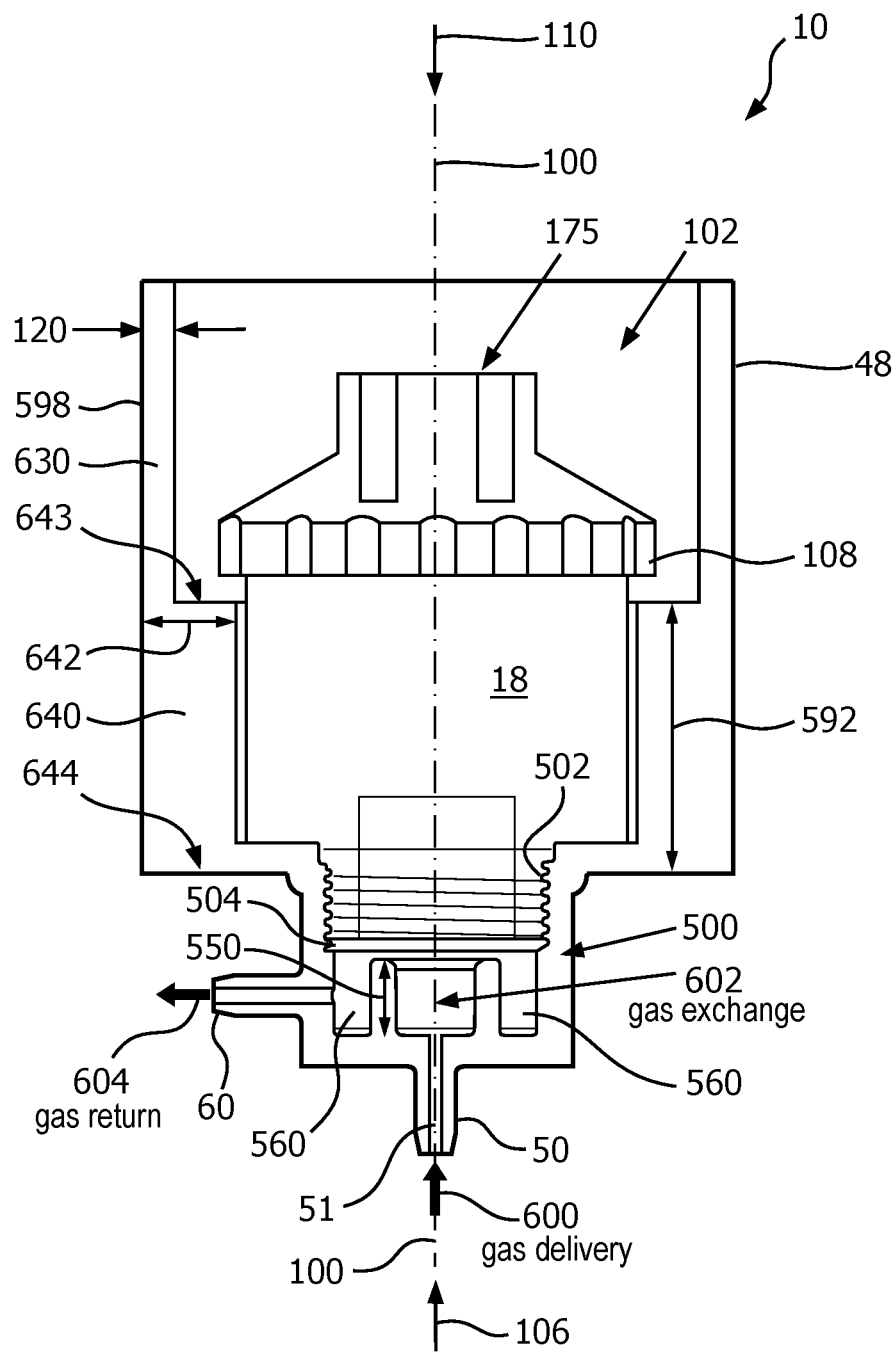
FIG. 6 is another cross-sectional view of the sensor coupled with the receiver body.

FIG. 6 illustrates another cross-sectional view of sensor 18 coupled with receiver body 48. FIG. 6 illustrates receiving gas 600 through delivery port 50 (e.g., from flow path 16 shown in FIG. 1-2), facilitating gas exchange 602 by guiding the received gas toward sensor face 500 via conduit 51, and returning 604 the sample back into system 8 (FIG. 1-2) via return port 60. In some embodiments, radial space 595 (shown in FIG. 5) is not included in apparatus 10. FIG. 6 illustrates that, in some embodiments, the wall thickness of wall 598 of second portion 114 of receiver body 48 is not constant. As shown in FIG. 6, wall 598 has a first portion 630 with wall thickness 120 (described above) and a second portion 640 with a wall thickness 642 that increases from a first end 643 of second portion 640 toward a second end 644 of second portion 640 (e.g., toward first end 106 of apparatus 10). It should be noted that the varying wall thickness 642 is not critical to the function of this invention. FIG. 6 shows these features for illustration purposes only. In practical use, these features may be cored out allowing for injection molding, and/or simply be a machined receiver, for example.

Figure 7:
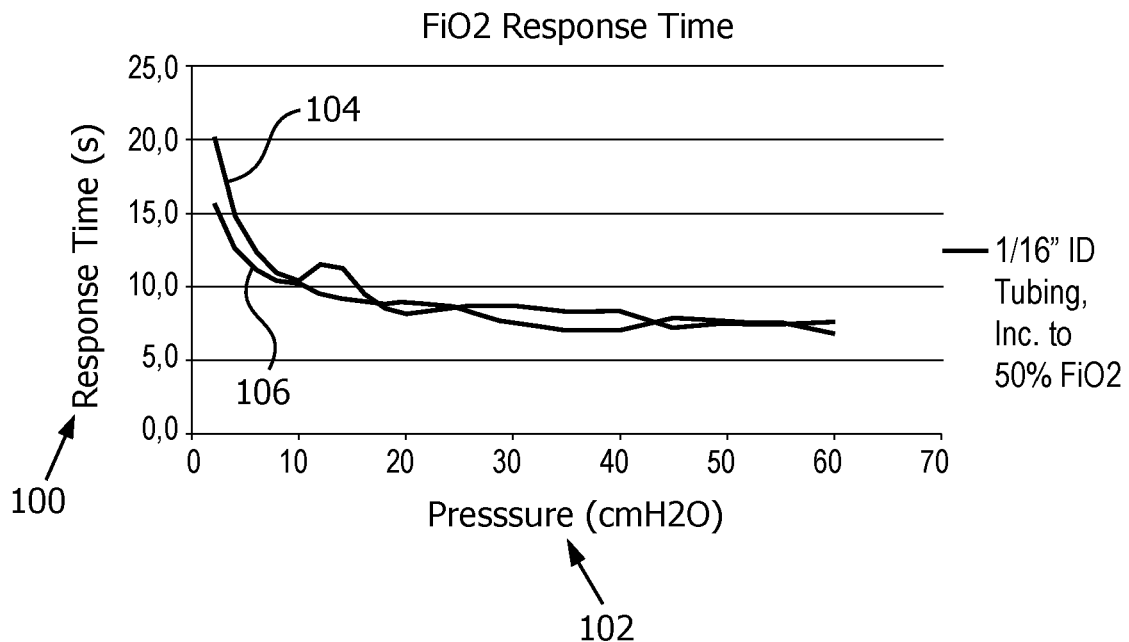
FIG. 7 shows an example of empirical data gathered using the sensor coupled to the apparatus with 1/16" inside diameter tubing coupling the apparatus to the system.

As described above related to FIG. 1, returning gas exhausted from apparatus 10 to a negative pressure area (e.g., through inlet 40 of pressure generator 14) of system 8 increases the pressure differential (e.g., <0 PSIG) and induces a faster sampling rate for sensor 18. FIG. 7 shows an example of empirical data gathered using sensor 18 coupled to apparatus 10 with 1/16" inside diameter tubing coupling apparatus 10 to system 8. In FIG. 7, vertical axis 700 shows the response time in seconds and horizontal axis 702 shows the outlet stream pressure. Line 704 indicates the response time while increasing the oxygen delivery through a control to 50%. Line 706 indicates decay of a 50% $O_2$ concentration back to ambient conditions of 21%. Accuracy was verified with a secondary, independent source in the outlet stream (e.g., as is typically monitored in prior art systems). FIG. 7 shows that the response time and accuracy of sensor 18 coupled with apparatus 10 in system 8 (as described herein) are well within electro-chemical sensor manufacturer specifications.

Returning to FIG. 1, controller 20 is configured to control pressure generator 14 to generate the flow of gas in accordance with a positive pressure support therapy regime. In positive airway pressure support therapy the pressurized flow of gas generated by the pressure generator is controlled to replace and/or compliment a patient's regular breathing. Positive airway pressure support therapy may be used to maintain an open airway in a patient so that oxygen and carbon dioxide may be exchanged more easily, requiring little and/or no effort from the patient. By way of non-limiting example, controller 20 may control pressure generator 14 such that the pressure support provided to the subject via the flow of gas comprises continuous positive airway pressure support (CPAP), bi-level positive airway pressure support (BPAP), proportional positive airway pressure support (PPAP), forced oscillation technique, and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation. In some therapy modes (e.g., PPAP), control module 54 may control pressure generator 14 to apply variable pressure support in which the amount of pressure delivered to the patient during inhalation and/or during exhalation is determined and delivered on a breath by breath basis. In some embodiments, controller 20 may be configured to control pressure generator 14 to temporarily drop the supplied pressure during exhalation (C-Flex) to reduce exhalation effort required by the patent.

In some embodiments, controller 20 is configured to control pressure generator 14 to deliver staged pressure support. In staged pressure support therapy, the pressure delivered by pressure generator 14 gradually increases over time. In some embodiments, controller 20 may control pressure generator 14 to switch therapy modes based on information related to the respiration of subject 12 and/or other information. For example, controller 20 may control pressure generator 14 to change from BPAP to CPAP after a certain number of breaths by subject 12.

Controller 20 is configured to control pressure generator 14 based on information related to the output signals from sensors 17, 18, information entered by a user to user interface 22, information stored in electronic storage 24, and/or other information.

User interface 22 is configured to provide an interface between system 8 and subject 12 and/or other users through which subject 12 and/or other users may provide information to and receive information from system 8. Other users may comprise, for example, a caregiver, a doctor, and/or other users. This enables data, cues, results, and/or instructions and any other communicable items, collectively referred to as "information," to be communicated between a user (e.g., subject 12) and one or more of pressure generator 14, controller 20, and/or other components of system 10. For example, a user may specify one or more therapy regimes that are to be delivered to subject 12 using user interface 22. Controller 20 may then customize the therapy regime delivered to subject 12 based on the one or more inputs made by the user to the user interface. As another example, therapy pressures, the breath rate of subject 12, and/or other information may be displayed to a user (e.g., subject 12) via user interface 22.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 22 comprises a plurality of separate interfaces. In one embodiment, user interface 22 comprises at least one interface that is provided integrally with pressure generator 14 and/or controller 20.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 8 and/or removable storage that is removably connectable to system 8 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 24 may store software algorithms, information determined by controller 20, information received via user interface 22, and/or other information that enables system 8 to function properly. Electronic storage 24 may be (in whole or in part) a separate component within system 8, or electronic storage 24 may be provided (in whole or in part) integrally with one or more other components of system 10 (e.g., user interface 22, controller 20, pressure generator 14, etc.).

Information determined by controller 20 and/or stored by electronic storage 24 may comprise information related to respiration of subject 12, compliance, use frequency, and/or other information. The information stored by electronic storage 24 may be viewed via user interface 22, and/or other via other methods. The information stored by electronic storage 24 may be used, for example, to adjust settings, used by a doctor to make medical decisions, and/or for other uses. In some embodiments, system 8 may include a wireless transmitter (not shown) and the information determined by controller 20, the information stored by electronic storage 24, and/or other information may be communicated to a care giver, for example, over a wireless network.

Figure 8:
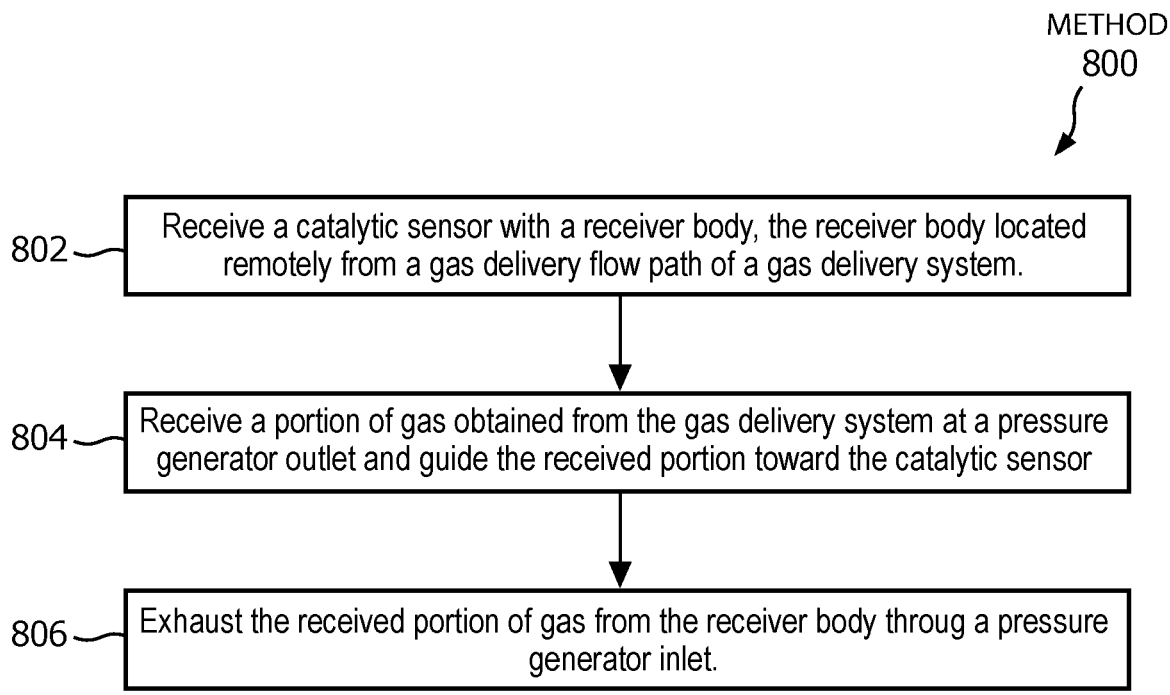
FIG. 8 illustrates a method to facilitate monitoring of gas in a therapeutic gas delivery system with a catalytic sensor and a monitoring apparatus.

FIG. 8 illustrates a method 800 to facilitate monitoring of gas in a therapeutic gas delivery system with a catalytic sensor and a monitoring apparatus. The monitoring apparatus comprises a receiver body, a delivery port, and a return port. The gas delivery system comprises a pressure generator having an inlet and an outlet, and a gas delivery flow path configured to communicate the gas between the pressure generator and a subject. The operations of method 800 presented below are intended to be illustrative. In some embodiments, method 800 may be accomplished with one or more additional operations not described, and/or without one or more of the operations discussed. Additionally, the order in which the operations of method 800 are illustrated in FIG. 8 and described below is not intended to be limiting.

In some embodiments, method 800 may be implemented in and/or controlled by one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 802, the catalytic sensor is received with the receiver body. The catalytic sensor is received such that the catalytic sensor removably couples with the receiver body. The receiver body is located remotely from the gas delivery flow path. In some embodiments, the receiver body is configured such that the catalytic sensor is received in an interior of the receiver body and the delivery port and the return port are formed on an exterior of the receiver body at a first end of the receiver body such that the delivery port, the return port, and a sensor face of the catalytic sensor are located in proximity to each other at or near the first end. In some embodiments, the catalytic sensor is an $O_2$ sensor and the receiver body is configured to receive the $O_2$ sensor such that the $O_2$ sensor is not in the gas delivery flow path of the gas delivery system. In some embodiments, operation 802 is performed by a receiver body the same as or similar to receiver body 48 (shown in FIG. 1 and described herein).

At an operation 804, a portion of gas obtained from the gas delivery system that has passed through the pressure generator outlet is received and guided toward the catalytic sensor. The portion of gas is received and guided by the delivery port. The delivery port is formed by the receiver body. In some embodiments, the delivery port receives the portion of gas from the gas delivery system via a first conduit having an inner diameter of about $\frac{1}{16}^{th}$ of an inch that couples the gas delivery system at or near the pressure generator outlet with the delivery port. In some embodiments, operation 804 is performed by a delivery port the same as or similar to delivery port 50 (shown in FIG. 1 and described herein).

At an operation 806, the received portion of gas is exhausted from the receiver body through the pressure generator inlet. The portion of gas is exhausted from the return port. The return port is formed by the receiver body. In some embodiments, the exhausted gas is returned to the gas delivery system via a second conduit having an inner diameter of about $\frac{1}{16}^{th}$ of an inch that couples the gas delivery system at or near the pressure generator inlet with the return port. In some embodiments, the delivery port and the catalytic sensor are located along an axis of the apparatus, and the return port is substantially perpendicular to the axis. In some embodiments, operation 806 is performed by a return port the same as or similar to return port 60 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. An apparatus configured to facilitate monitoring of gas in a therapeutic gas delivery system with a catalytic sensor; the gas delivery system comprising a pressure generator having an inlet and an outlet, and a gas delivery flow path configured to communicate the gas between the pressure generator and a subject; the apparatus comprising:
a receiver body configured to receive the catalytic sensor such that the catalytic sensor removably couples with the receiver body, the receiver body located outside the gas delivery flow path;
a delivery port formed by the receiver body configured to receive a portion of gas obtained from the gas delivery system that has passed through the pressure generator outlet and guide the received portion of gas through the catalytic sensor; and
a return port formed by the receiver body configured to exhaust the received portion of gas guided through the catalytic sensor from the receiver body, the return port coupled to the gas delivery system such that the exhausted gas is returned to the gas delivery system through the pressure generator inlet without flowing through the gas delivery flow path.

2. The apparatus of claim 1, wherein the delivery port is configured to receive the portion of gas from the gas delivery system via a first conduit having an inner diameter that couples the gas delivery system at or near the pressure generator outlet with the delivery port; and wherein, the return port is configured to return the exhausted gas to the gas delivery system via a second conduit having an inner diameter that couples the gas delivery system at or near the pressure generator inlet with the return port.

3. The apparatus of claim 1, wherein the delivery port and the catalytic sensor are located along an axis of the apparatus, and wherein the return port is substantially perpendicular to the axis.

4. The apparatus of claim 1, wherein the receiver body is configured to receive the catalytic sensor in an interior of the receiver body, and wherein the delivery port and the return port are formed on an exterior of the receiver body toward a first end of the receiver body such that the delivery port, the return port, and a sensor face of the catalytic sensor are located at or near the first end.

5. The apparatus of claim 1, wherein the catalytic sensor is an $O_2$ sensor and the receiver body is configured to receive the $O_2$ sensor such that the $O_2$ sensor is not in the gas delivery flow path of the gas delivery system.

6. A method to facilitate monitoring of gas in a therapeutic gas delivery system with a catalytic sensor and a monitoring apparatus; the monitoring apparatus comprising a receiver body, a delivery port, and a return port; the gas delivery system comprising a pressure generator having an inlet and an outlet, and a gas delivery flow path configured to communicate the gas between the pressure generator and a subject; the method comprising:
receiving, with the receiver body, the catalytic sensor such that the catalytic sensor removably couples with the receiver body, the receiver body located outside the gas delivery flow path;
receiving, with the delivery port, a portion of gas obtained from the gas delivery system that has passed through the pressure generator outlet and guide the received portion of gas through the catalytic sensor, the delivery port formed by the receiver body; and
exhausting, with the return port, the received portion of gas guided through the catalytic sensor from the receiver body, the return port coupled to the gas delivery system such that the exhausted gas is returned to the gas delivery system through the pressure generator inlet without flowing through the gas delivery flow path, the return port formed by the receiver body.

7. The method of claim 6, further comprising receiving, with the delivery port, the portion of gas from the gas delivery system via a first conduit having an inner diameter that couples the gas delivery system at or near the pressure generator outlet with the delivery port; and returning, with the return port, the exhausted gas to the gas delivery system via a second conduit having an inner diameter that couples the gas delivery system at or near the pressure generator inlet with the return port.

8. The method of claim 6, further comprising locating the delivery port and the catalytic sensor along an axis of the apparatus, wherein the return port is substantially perpendicular to the axis.

9. The method of claim 6, further comprising receiving, with the receiver body, the catalytic sensor in an interior of the receiver body, and forming the delivery port and the return port on an exterior of the receiver body toward a first end of the receiver body such that the delivery port, the return port, and a sensor face of the catalytic sensor are located at or near the first end.

10. The method of claim 6, wherein the catalytic sensor is an $O_2$ sensor and the receiver body is configured to receive the $O_2$ sensor such that the $O_2$ sensor is not in the gas delivery flow path of the gas delivery system.

11. An apparatus configured to facilitate monitoring of gas in a therapeutic gas delivery system with a catalytic sensor; the gas delivery system comprising a pressure generator having an inlet and an outlet, and a gas delivery flow path configured to communicate the gas between the pressure generator and a subject; the apparatus comprising:
means for receiving the catalytic sensor such that the catalytic sensor removably couples with the means for receiving the catalytic sensor, the means for receiving the catalytic sensor located outside the gas delivery flow path;
means, formed by the means for receiving the catalytic sensor, for receiving a portion of gas obtained from the gas delivery system that has passed through the pressure generator outlet and guiding the received portion of gas through the catalytic sensor; and
means, formed by the means for receiving the catalytic sensor, for exhausting the received portion of gas guided through the catalytic sensor from the means for receiving the catalytic sensor, the means for exhausting coupled to the gas delivery system such that the exhausted gas is returned to the gas delivery system through the pressure generator inlet without flowing through the gas delivery flow path.

12. The apparatus of claim 11, wherein the means for receiving and guiding is configured to receive the portion of gas from the gas delivery system via a first conduit having an inner diameter that couples the gas delivery system at or near the pressure generator outlet with the means for receiving and guiding; and wherein, the means for exhausting, is configured to return the exhausted gas to the gas delivery system via a second conduit having an inner diameter that couples the gas delivery system at or near the pressure generator inlet with the means for exhausting.

13. The apparatus of claim 11, wherein the means for receiving and guiding and the catalytic sensor are located along an axis of the apparatus, and wherein the means for exhausting is substantially perpendicular to the axis.

14. The apparatus of claim 11, wherein the means for receiving the catalytic sensor is configured to receive the catalytic sensor in an interior of the means for receiving the catalytic sensor, and wherein the means for receiving and guiding and the means for exhausting are formed on an exterior of the means for receiving the catalytic sensor toward a first end of the means for receiving the catalytic sensor such that the means for receiving and guiding, the means for exhausting, and a sensor face of the catalytic sensor are located at or near the first end.

15. The apparatus of claim 11, wherein the catalytic sensor is an $O_2$ sensor and the means for receiving the catalytic sensor is configured to receive the $O_2$ sensor such that the $O_2$ sensor is not in the gas delivery flow path of the gas delivery system.

16. A therapeutic gas delivery system comprising:
a pressure generator having an inlet and an outlet configured to generate a pressurized flow of breathable gas for delivery to an airway of a subject;
a gas delivery flow path configured to communicate the gas between the pressure generator and the subject;
a catalytic sensor configured to generate one or more output signals that convey information related to one or more parameters of the gas; and
a monitoring apparatus, the apparatus comprising:
a receiver body configured to receive the catalytic sensor such that the catalytic sensor removably couples with the receiver body, the receiver body located outside the gas delivery flow path,
a delivery port formed by the receiver body configured receive a portion of gas that has passed through the pressure generator outlet and guide the received portion of gas through the catalytic sensor, and
a return port formed by the receiver body configured to exhaust the received portion of gas guided through the catalytic sensor from the receiver body, the return port coupled to the gas delivery system such that the exhausted gas is returned to the gas delivery system through the pressure generator inlet without flowing through the gas delivery flow path.

17. The system of claim 16, wherein the delivery port is configured to receive the portion of gas via a first conduit having an inner diameter that couples the gas delivery flow path at or near the pressure generator outlet with the delivery port, and wherein, the return port is configured to return the exhausted gas to the gas delivery flow path via a second conduit having an inner diameter that couples the gas delivery flow path at or near the pressure generator inlet with the return port.

18. The system of claim 16, wherein the delivery port and the catalytic sensor are located along an axis of the apparatus, and wherein the return port is substantially perpendicular to the axis.

19. The system of claim 16, wherein the receiver body is configured to receive the catalytic sensor in an interior of the receiver body, and wherein the delivery port and the return port are formed on an exterior of the receiver body toward a first end of the receiver body such that the delivery port, the return port, and a sensor face of the catalytic sensor are located at or near the first end.

20. The system of claim 16, wherein the catalytic sensor is an $O_2$ sensor and the receiver body is configured to receive the $O_2$ sensor such that the $O_2$ sensor is not in the gas delivery flow path of the gas delivery system.

21. The apparatus of claim 1, wherein the catalytic sensor comprises a threaded connection and an O-ring portion for removably coupling with the receiver body.

22. The apparatus of claim 21, wherein the receiver body comprises a sensor seating guide configured to guide the catalytic sensor into the receiver body such that the threaded connection aligns with threads on an inner surface of the receiver body.

23. The method of claim 6, wherein the catalytic sensor comprises a threaded connection and an O-ring portion for removably coupling with the receiver body.

24. The method of claim 23, wherein the receiver body comprises a sensor seating guide configured to guide the catalytic sensor into the receiver body such that the threaded connection aligns with threads on an inner surface of the receiver body.

25. The apparatus of claim 11, wherein the catalytic sensor comprises a threaded connection and an O-ring portion for removably coupling with the means for receiving.

26. The apparatus of claim 25, wherein the means for receiving comprises sensor seating guide means configured to guide the catalytic sensor into the means for receiving such that the threaded connection aligns with threads on an inner surface of the means for receiving.

27. The system of claim 16, wherein the catalytic sensor comprises a threaded connection and an O-ring portion for removably coupling with the receiver body.

28. The system of claim 27, wherein the receiver body comprises a sensor seating guide configured to guide the catalytic sensor into the receiver body such that the threaded connection aligns with threads on an inner surface of the receiver body.

* * * * *